(12) United States Patent
Endo et al.

(10) Patent No.: US 7,860,562 B2
(45) Date of Patent: Dec. 28, 2010

(54) EXTERNAL FORCE CONTROL METHOD, EXTERNAL FORCE CONTROL SYSTEM AND EXTERNAL FORCE CONTROL PROGRAM

(75) Inventors: Yosuke Endo, Wako (JP); Ritsuo Hara, Wako (JP)

(73) Assignee: Honda Motor Co., Ltd., Tokyo (JP)

(*) Notice: Subject to any disclaimer, the term of this patent is extended or adjusted under 35 U.S.C. 154(b) by 190 days.

(21) Appl. No.: 10/599,808

(22) PCT Filed: Nov. 29, 2005

(86) PCT No.: PCT/JP2005/021879
§ 371 (c)(1),
(2), (4) Date: Oct. 10, 2006

(87) PCT Pub. No.: WO2006/064657
PCT Pub. Date: Jun. 22, 2006

(65) Prior Publication Data
US 2008/0139968 A1 Jun. 12, 2008

(30) Foreign Application Priority Data
Dec. 16, 2004 (JP) ............................. 2004-365056

(51) Int. Cl.
*A61B 5/04* (2006.01)
(52) U.S. Cl. .............................. 600/546; 600/595; 601/5
(58) Field of Classification Search .................... 623/24, 623/25; 600/595, 564
See application file for complete search history.

(56) References Cited

U.S. PATENT DOCUMENTS 3,418,662 A * 12/1968 Bottomley et al. ............ 623/25

(Continued)

FOREIGN PATENT DOCUMENTS

EP 1324403 * 11/2002

(Continued)

*Primary Examiner*—Max Hindenburg
*Assistant Examiner*—Renee Danega
(74) *Attorney, Agent, or Firm*—Rankin, Hill & Clark LLP (57) ABSTRACT

A method of controlling an external force applied to an animal to achieve as a target relation the relation between the external force and a motion variable varying with the motion of the animal. A value of an external force f applied to a human leg according to an external force function f(x) on the basis of a measured value of a myoelectric potential x that occurs in the human leg, current I of a motor 220 is controlled according to the set value, and the external force f is applied to the leg through an orthosis 222. A resultant force (the sum of an internal torque and an external torque around a knee joint) F is measured as "a motion variable." Moreover, a value of a factor $\gamma$ is set according to a factor function $\gamma(f, F)$ on the basis of the set value of the external force f and the measured value of the resultant force F. If a deviation $\delta$ between the set value of the factor $\gamma$ and target value $\gamma_t$ thereof is equal to or greater than a reference value $\epsilon$, a new external force function f(x) is set in such a way that the set value of the factor $\gamma$ approaches the target value $\gamma_t$.

19 Claims, 5 Drawing Sheets

U.S. PATENT DOCUMENTS

| | | | |
|---|---|---|---|
| 5,413,611 A * | 5/1995 | Haslam et al. | 623/25 |
| 6,660,042 B1 * | 12/2003 | Curcie et al. | 623/24 |
| 6,740,123 B2 * | 5/2004 | Davalli et al. | 623/24 |
| 7,367,958 B2 * | 5/2008 | McBean et al. | 602/16 |
| 2004/0106881 A1 * | 6/2004 | McBean et al. | 601/5 |
| 2004/0107780 A1 * | 6/2004 | Kawai et al. | 73/862.08 |

FOREIGN PATENT DOCUMENTS

| | | |
|---|---|---|
| JP | 2001-286451 | 10/2001 |
| JP | 2003-079684 | 3/2003 |
| JP | 2003-089083 | 3/2003 |
| JP | 2003-116893 | 4/2003 |
| JP | 2004-073649 | 3/2004 |
| JP | 2004-105261 | 4/2004 |
| JP | 2004-167056 | 6/2004 |
| JP | 2005-095561 | 4/2005 |

* cited by examiner

RECTUS FEMORIS
VASTUS LATERALIS
VASTUS MEDIALIS
111

FIG.2(b)

SEMITENDINOSUS
BICEPS FEMORIS
112

EXTERNAL FORCE CONTROL METHOD, EXTERNAL FORCE CONTROL SYSTEM AND EXTERNAL FORCE CONTROL PROGRAM

TECHNICAL FIELD

The present invention relates to a method and system for controlling an external force applied to an animal through an orthosis attached to the animal that makes a movement along with the activities of muscle fibers and a program for providing a computer with the control functions.

BACKGROUND ART

An external force applied to a person with the purpose of walking aid is preferably controlled to an appropriate one in relation to an internal force that arises due to his or her will according to the progress of rehabilitation exercise or the like. Therefore, it is conceivable to measure a joint torque on the basis of a myoelectric signal that occurs in a human body and to apply a torque (external force) of an appropriate level according to the joint torque to the person.

Conventionally, there has been suggested a technology of estimating a muscle force of a leg by an output from a pressure sensor or the like attached to the toe or heel of a sole and applying a support force to the leg through the device attached to the leg for reducing a load on muscles of the leg if the muscle force is greater than a reference value (for example, refer to paragraphs 0006 to 0012 and FIGS. 1 to 4 of Japanese Patent Laid-Open No. 2004-105261). Moreover, there has been suggested a technology of measuring a myoelectric signal that occurs in a human body and measuring a joint torque or the like of the animal concerned based on the myoelectric signal (for example, refer to paragraphs 0038 to 0062 of Japanese Patent Laid-Open No. 2001-286451).

If there is any change in muscle fatigue degree or in the contact condition between electrodes and the body due to perspiration or the like, it is projected that the relation between the myoelectric signal and the joint torque changes even in the same person and that simply adopting the conventional technologies does not provide a desired force applied to the person based on the myoelectric signal.

Therefore, the object of the present invention is to provide a method and system capable of controlling an external force applied to an animal in such a way as to achieve as a target relation the relation between the external force and a motion variable varying with the motion of the animal and a program for providing a computer with the control functions.

DISCLOSURE OF THE INVENTION

According to one aspect of the present invention to resolve the above problem, there is provided an external force control method for controlling an external force applied to an animal through an orthosis attached to the animal that makes a movement along with the activities of muscle fibers, the method comprising: a myoelectric potential measurement step of measuring a myoelectric potential x that occurs in the body of the animal; an external force setting step of setting a value of an external force f applied to the animal through the orthosis according to an external force function f(x) with the myoelectric potential x as a variable on the basis of the measured value of the myoelectric potential x; a motion variable measurement step of measuring a motion variable y varying with the motion of the animal under the condition of the external force applied through the orthosis; a factor setting step of setting a value of a factor $\gamma$ according to a factor function $\gamma(f, y)$ with the external force f and the motion variable y as variables on the basis of the set value of the external force f and the measured value of the motion variable y; a determination step of determining whether a deviation $\delta$ between the set value of the factor $\gamma$ and target thereof value $\gamma_t$ is less than a reference value $\epsilon$; and an external force function setting step of setting a new external force function f(x) in such a way that the set value of the factor $\gamma$ approaches the target value $\gamma_t$ if the deviation $\delta$ is determined to be equal to or greater than the reference value $\epsilon$ in the determination step.

According to the external force control method of the present invention, the value of the external force f is set according to the external force function f(x) on the basis of the measured value of the myoelectric potential x and the external force applied to the animal is controlled through the orthosis according to the set value of the external force f. Moreover, the motion variable y varying with the motion of the animal is measured under the condition of the external force applied through the orthosis and the value of the factor $\gamma$ is set according to a factor function $\gamma(f, y)$ on the basis of the set value of the external force f and the measured value of the motion variable y. Furthermore, it is determined whether the deviation $\delta$ between the set value of the factor $\gamma$ and its target value $\gamma_t$ is less than the reference value $\epsilon$. Then, if the deviation $\delta$ is determined to be equal to or greater than the reference value $\epsilon$, a new external force function f(x) is set in such a way that the set value of the factor $\gamma$ approaches the target value $\gamma_t$. The deviation $\delta$ includes a deviation at a certain time point and a mean deviation or cumulative deviation at a plurality of time points or during a continuous time period. This controls the external force f in such a way that the value of the factor $\gamma$ approaches the target value $\gamma_t$.

The factor $\gamma$ set according to the factor function $\gamma(f, y)$ with the external force f and the motion variable y as variables represents what kind of relation exists between the external force f and the motion variable y. In addition, the target value $\gamma_t$ of the factor $\gamma$ represents what kind of target relation exists between the external force f and the motion variable y.

Therefore, according to the external force control method of the present invention, it is possible to control the external force f on the basis of the myoelectric potential x in such a way that the relation between the external force f and the motion variable y approaches the target relation ($\gamma_t = \gamma(f, y)$), which is determined according to the factor target value $\gamma_t$, even if any change occurs in the myoelectric potential measurements of the animal.

The myoelectric potential x can be either one of a myoelectric potential or a combination of a plurality of myoelectric potentials $\{x_i | i=1, 2, ---\}$. Furthermore, the external force f can be either one of an external force or a combination of a plurality of external forces $\{f_i | i=1, 2, ---\}$. Still further, the motion variable y can be either one of the motion variable or a combination of a plurality of motion variables $\{y_i | i=1, 2, ---\}$. Moreover, the factor $\gamma$ can be either one of a factor or a combination of a plurality of factors $\{y_i | i=1, 2, ---\}$.

In the external force control method according to the present invention, the external force function setting step includes setting a value of a coefficient $\alpha$ that represents the relation between the myoelectric potential x and the external force f and setting the external force function f(x) according to a basic function $F(x, \alpha)$ with the myoelectric potential x and the coefficient $\alpha$ as variables on the basis of the set value of the coefficient $\alpha$.

According to the external force control method of the present invention, a new value is set for the coefficient $\alpha$ that represents the relation between the myoelectric potential x and the external force f if the deviation between the set value of the factor $\gamma$ and its target value $\gamma_t$ is equal to or greater than the reference value $\epsilon$. Moreover, a new value is set for the external force function f(x) according to the basic function F(x, α) on the basis of the new set value of the coefficient α. Thereafter, the external force f applied to the animal is set according to the new external force function f(x) on the basis of the measured value of the myoelectric potential x. This enables the external force f to be controlled based on the measured value of the myoelectric potential x in such a way that the relation between the external force f and the motion variable y approaches the target relation on the basis of the latest relation between the myoelectric potential x and the external force f even if any change occurs in the myoelectric potential measurements of the animal. The coefficient α can be either one of a coefficient or a combination of a plurality of coefficients $\{\alpha_i | i=1, 2, ---\}$.

Furthermore, in the external force control method according to the present invention, the external force function setting step includes finding the external force target value $f_t$ according to the factor function $\gamma(f, y)$ on the basis of the measured value of the motion variable y and the target value $\gamma_t$ of the factor $\gamma$ and setting the external force function f(x) in such a way that the external force f approaches the external force target value $f_t$.

According to the external force control method of the present invention, the external force f set based on the myoelectric potential x and applied to the animal can be controlled in such a way as to approach the target value $f_t$ responsive to the target relation ($\gamma_t = \gamma(f, y)$), which depends on the target value $\gamma_t$ of the factor $\gamma$, even if any change occurs in the myoelectric potential measurements of the animal.

Furthermore, in the external force control method according to the present invention, the external force function setting step includes setting the external force function f(x) in such a way that a maximum measured value of the external force f approaches a maximum value of the external force target value $f_t$.

According to the external force control method of the present invention, the external force f applied to the animal can be controlled in such a way that the maximum measured value of the external force f approaches the maximum value of the target value $f_t$. The "maximum value" of the measured value of the external force f and of the target value $f_t$ respectively includes the maximum value during a certain time zone and further the maximum value of the measured value of the external force f and of the target value $f_t$ in each period in the case of a periodic variation in the measured value of the external force f and in the target value $f_t$.

Furthermore, in the external force control method according to the present invention, the determination step is omitted and the external force function setting step is performed after the first external force setting step.

According to the external force control method of the present invention, the new external force function f(x) is set without passing through the determination in view of the fact that it is highly probable that the first set value of the external force f is far from the target relation between the external force f and the motion variable y since the first external force function f(x) does not yet reflect the actual relation between the external force f and the motion variable y. This enables the external force f to be controlled in such a way that the relation between the external force f and the motion variable y rapidly approaches the target relation.

Still further, in the external force control method according to the present invention, the motion variable measurement step includes measuring the resultant force of an internal force and an external force of the animal as the motion variable y and the factor setting step includes setting the ratio of the external force f to the resultant force of the internal force and the external force of the animal as the factor $\gamma$ ($0 \leq \gamma < 1$).

Furthermore, in the external force control method according to the present invention, the motion variable measurement step includes measuring a primitive motion variable varying with the motion of the animal and measuring the motion variable according to the inverse dynamics model that represents the behaviors of the animal on the basis of the measured value of the primitive motion variable.

Furthermore, the external force control method according to the present invention further includes a motion state determination step of determining the motion state of the animal according to a given correspondence between the primitive motion variable and the motion state of the animal on the basis of the measured value of the primitive motion variable after measuring the primitive motion variable varying with the motion of the animal, wherein the motion variable measurement step includes measuring the motion variable y according to a given correspondence between the motion state of the animal and the motion variable on the basis of the motion state determined in the motion state determination step.

Furthermore, the external force control method according to the present invention further includes a step of measuring the external force f, wherein the factor setting step includes setting a value of the factor $\gamma$ according to the factor function $\gamma(f, y)$ with the external force f and the motion variable y as variables on the basis of the measured value of the external force f, instead of the set value of the external force f, and the measured value of the motion variable y.

According to the external force control method of the present invention, the factor $\gamma$ is set on the basis of the measured value of the external force f, and therefore it is possible to control the external force f applied to the animal after removing the effect of the deviation that may occur in the measured value of the external force f from the set value of the external force f.

Furthermore, the external force control method according to the present invention further includes a motion state determination step of determining the motion state of the animal according to the given correspondence between the primitive motion variable and the motion state of the animal on the basis of the measured value of the primitive motion variable after measuring the primitive motion variable varying with the motion of the animal, wherein the external force function setting step includes setting a new external force function f(x) responsive to each motion state determined in the motion state determination step.

Furthermore, in the external force control method according to the present invention further, the determination step includes determining whether the deviation δ is less than the reference value $\epsilon$ on the basis of the factor target value $\gamma_t$ set for each motion state according to the motion state determined in the motion state determination step and the external force function setting step includes setting a new external force function f(x) on the basis of the factor target value $\gamma_t$ set for each motion state according to the motion state determined in the motion state determination step.

According to the external force control method of the present invention, it is possible to achieve the appropriate external force f, which is set in the external force setting step and applied to the body of the animal with consideration given to the motion state of the animal.

Furthermore, in the external force control method of the present invention, the determination step includes determining whether the deviation δ is less than a threshold ε according to the threshold ε depending on whether the deviation δ is positive or negative.

According to the external force control method of the present invention, it is possible to control the external force f in such a way that if the instability level of the motion of the animal undergoing the external force f depends on whether the deviation δ between the set value of the factor γ and its target value $γ_t$ is positive or negative, the motion of the animal is stable with consideration given to the difference between them.

According to another aspect of the present invention to resolve the above problem, there is provided an external force control system for controlling an external force applied to an animal through an orthosis attached to the animal that makes a movement along with the activities of muscle fibers, the system comprising: myoelectric potential measurement means for measuring a myoelectric potential x that occurs in the body of the animal; external force setting means for setting a value of an external force f applied to the animal through the orthosis according to an external force function f(x) with the myoelectric potential x as a variable on the basis of the measured value of the myoelectric potential x measured by the myoelectric potential measurement means; motion variable measurement means for measuring a motion variable y varying with the motion of the animal under the condition of the external force applied through the orthosis; factor setting means for setting a value of a factor γ according to a factor function γ(f, y) with the external force f and the motion variable y as variables on the basis of the set value of the external force f set by the external force setting means and the measured value of the motion variable y measured by the motion variable measurement means; determination means for determining whether a deviation δ between the set value of the factor γ set by the factor setting means and target value $γ_t$ thereof is less than a reference value ε; and external force function setting means for setting a new external force function f(x) in such a way that the set value of the factor γ approaches its target value $γ_t$ if the deviation δ is determined to be equal to or greater than the reference value ε by the determination means.

According to the external force control system of the present invention, it is possible to control the external force f based on the myoelectric potential x in such a way that the relation between the external force f and the motion variable y approaches the target relation ($γ_t$=γ(f, y)), which is determined according to the factor target value $γ_t$, even if any change occurs in the myoelectric potential measurements of the animal.

According to still another aspect of the present invention to resolve the above problem, there is provided an external force control program for providing a computer with functions for controlling an external force applied to an animal through an orthosis attached to the animal that makes a movement along with the activities of muscle fibers, the program providing a computer with: a myoelectric potential measurement function of measuring a myoelectric potential x that occurs in the body of the animal; an external force setting function of setting a value of an external force f applied to the animal through the orthosis according to an external force function f(x) with the myoelectric potential x as a variable on the basis of the measured value of the myoelectric potential x; a motion variable measurement function of measuring a motion variable y varying with the motion of the animal under the condition of the external force applied through the orthosis; a factor setting function of setting a value of a factor γ according to a factor function γ(f, y) with the external force f and the motion variable y as variables on the basis of the set value of the external force f and the measured value of the motion variable y; a determination function of determining whether a deviation δ between the set value of the factor γ and target value $γ_t$ thereof is less than a reference value ε; and an external force function setting function of setting a new external force function f(x) in such a way that the set value of the factor γ approaches its target value $γ_t$ if the deviation δ is determined to be equal to or greater than the reference value ε by the determination function.

According to the external force control program of the present invention, it is possible to provide the computer with the functions for controlling the external force f based on the myoelectric potential x in such a way that the relation between the external force f and the motion variable y approaches the target relation ($γ_t$=γ(f, y)) determined according to the factor target value $γ_t$, even if any change occurs in the myoelectric potential measurements of the animal.

BEST MODE FOR CARRYING OUT THE INVENTION

Preferred embodiments of an external force control method, an external force control system, and an external force control program according to the present invention will be described by using the accompanying drawings.

Figure 1:
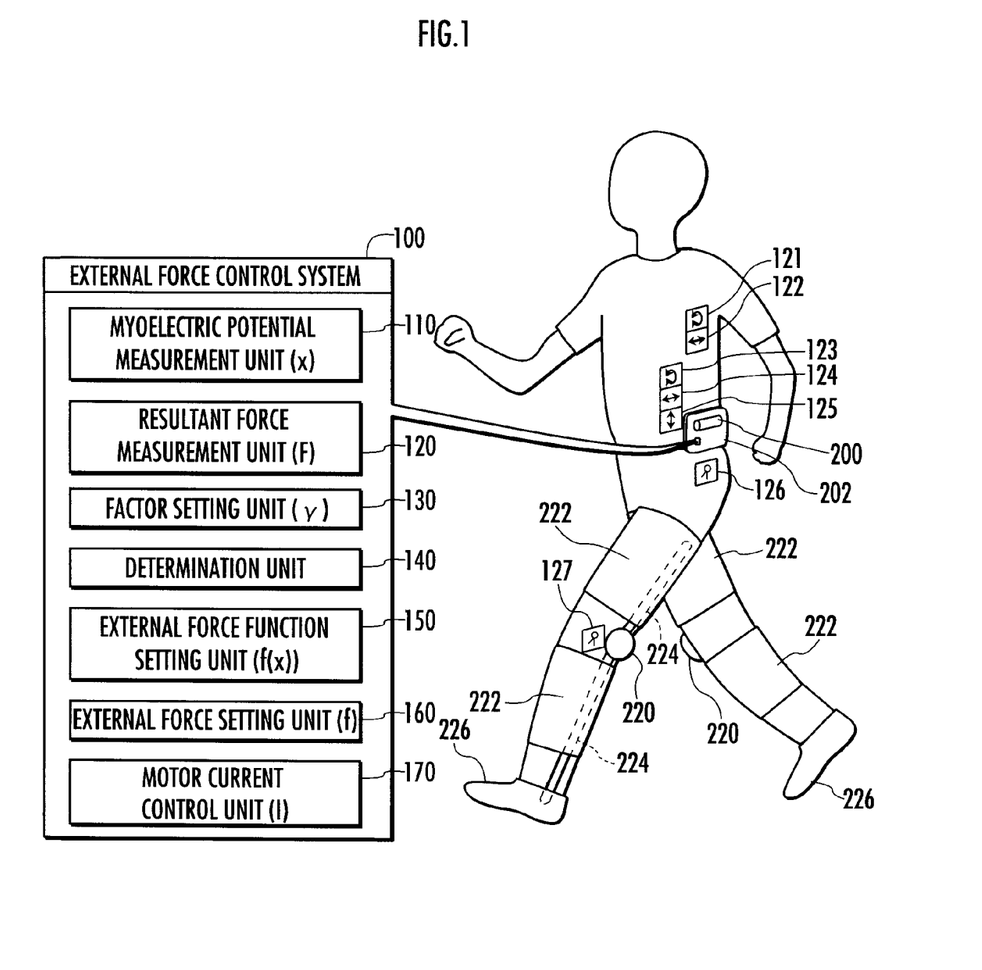
FIG. 1 is a configuration explanatory view of an external force control system according to one embodiment of the present invention.

The following describes the configuration of the external force control system in one embodiment of the present invention with reference to FIG. 1 and FIG. 2.

An external force control system 100 shown in FIG. 1 controls external torques (external forces) around the knee joints of a person (animal) applied to both left and right legs through orthoses 222 attached to the thigh and crus of the legs by means of motors (engines) 220 disposed on the person's left and right knees, respectively. The motors 220 work with a battery 200 as a power supply, which is contained in a case 202 attached to the waist.

The external force control system 100 includes a myoelectric potential measurement unit 110, a resultant force measurement unit (motion variable measurement means) 120, a factor setting unit 130, a determination unit 140, an external force function setting unit 150, an external force setting unit 160, and a motor current control unit 170. Each unit is made up of a computer 10 including a CPU as hardware, a memory such as an EEPROM or RAM, an I/O circuit and "an external force control program" of the present invention stored in the memory as software. The computer 10 works with the battery 200 as a power supply and is contained in the case 202.

Figure 2A:
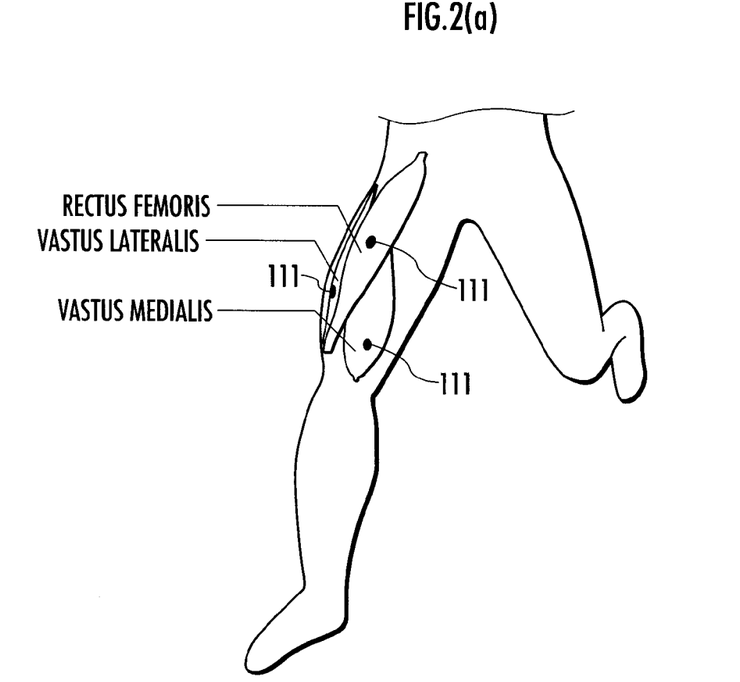
FIG. 2 is an explanatory view of a myoelectric potential measuring method.
Figure 2B:
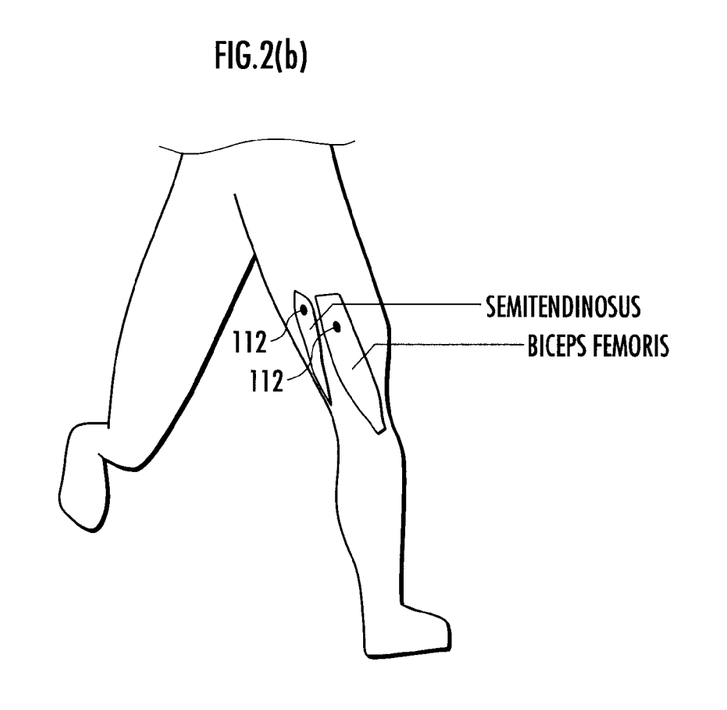

The myoelectric potential measurement unit 110 measures a myoelectric potential x through extensor surface electrodes 111, each of which are attached to a region of a vastus medialis, a vastus lateralis, and a rectus femoris (extensor) on the surface of the human body as shown in FIG. 2(a) and flexor surface electrodes 112, each of which are attached to a region of a semitendinosus and a biceps femoris (flexor) on the surface of the human body as shown in FIG. 2(b).

The resultant force measurement unit 120 includes a chest gyro sensor 121 for outputting a signal responsive to a tilt angular velocity of a human chest, an anteroposterior chest acceleration sensor 122 for outputting a signal responsive to an anteroposterior acceleration of the chest, a waist gyro sensor 123 for outputting a signal responsive to a tilt angular velocity of the waist, an anteroposterior waist acceleration sensor 124 for outputting a signal responsive to an anteroposterior acceleration of the waist, a vertical waist acceleration sensor 125 for outputting a signal responsive to a vertical acceleration of the waist, a hip joint angle sensor 126 for outputting a signal responsive to a flexion angle of a hip joint, and a knee joint angle sensor 127 for outputting a signal responsive to a flexion angle of a knee joint. The resultant force measurement unit 120 measures a resultant force F, which is the sum of an internal torque (internal force) around the knee joint that arises in the leg due to the person's will and an external torque (external force) around the knee joint given to the leg by the motor 220 disposed to the knee portion, as "a motion variable" on the basis of outputs from the sensors 121 to 127 and measured values of "primitive motion variables" such as a tilt angular velocity of the human chest or the like by using an inverse dynamics model that represents human behaviors. The power of the motor 220 is supplied to each leg through rigid members 224 connected to the motor 220 and extended upwardly and downwardly from the knee portion respectively, supporters (orthoses) 222 connected to the rigid members 224 and attached to the thigh portion and the crus portion, respectively, and a shoe 226 connected to the rigid member 224 extended downwardly from the knee portion. The inverse dynamics model is stored in the memory of the computer 10.

Figure 5:
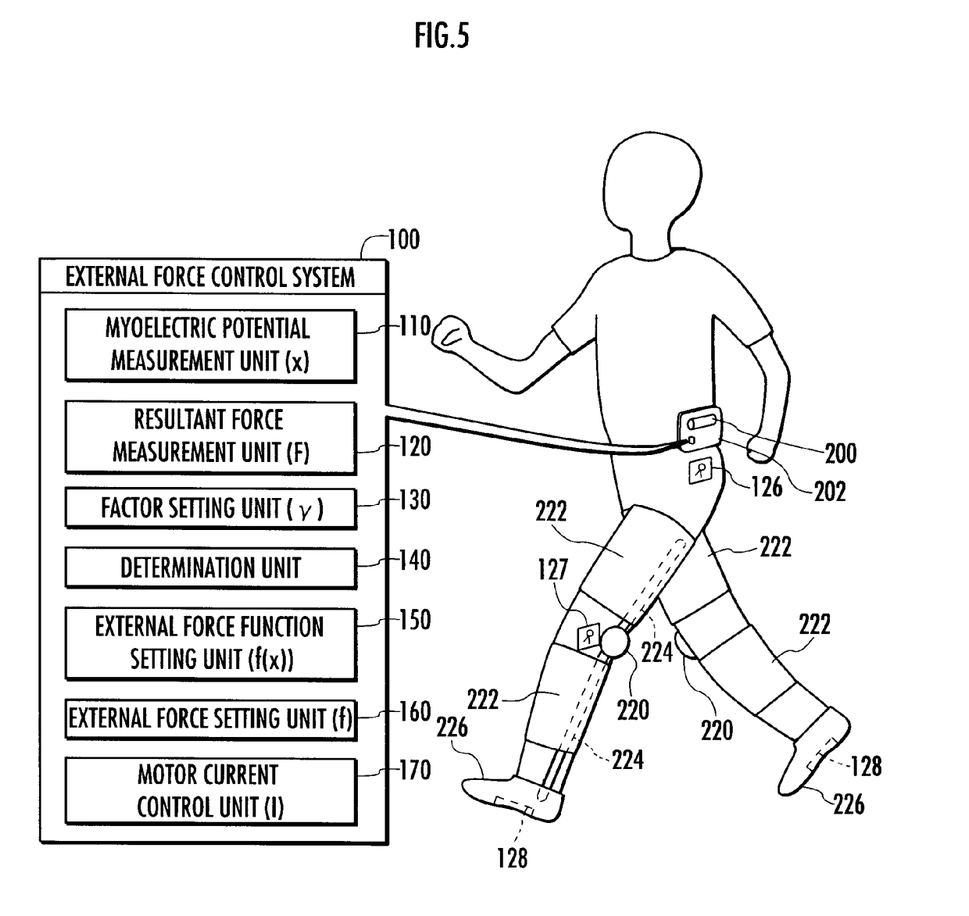
FIG. 5 is a configuration explanatory view of an external force control system according to another embodiment of the present invention.

As shown in FIG. 5, it is also possible to provide a floor reaction force sensor 128 for outputting a signal responsive to a floor reaction force applied to the sole of foot at the bottom of the shoe 226 with the omission of the sensors 121 to 125 in order to measure the resultant force F according to the inverse dynamics model on the basis of the outputs from the hip joint angle sensor 126, the knee joint angle sensor 127, and the floor reaction force sensor 128.

The factor setting unit 130 sets the factor γ according to the factor function γ(f, F) with the external force f and the resultant force (motion variable) F as variables on the basis of the set value of the external force f set by the external force setting unit 160 and the measured value of the resultant force F measured by the resultant force measurement unit 120.

The determination unit 140 determines whether the deviation δ between the measured value of the factor γ and its target value $\gamma_t$ is less than a threshold ε (>0). The target value $\gamma_t$ of the factor γ is stored in the memory of the computer 10. The target value $\gamma_t$ of the factor γ can be adjusted according to a person's (user's) intention through buttons (not shown) provided in the case 202.

The external force function setting unit 150 sets an external force target value $f_t$ as the product of a measured value of the resultant force F and the factor target value $\gamma_t$ and sets a coefficient α that represents the relation between the myoelectric potential x and the external force f in such a way that the set value of the external force f is coincident with the external force target value $f_t$. Moreover, the external force function setting unit 150 sets an external force function f(x), which is a function of the myoelectric potential x, according to a basic function F(x, α, γ) on the basis of the set value of the factor γ set by the factor setting unit 130 and the set value of the coefficient α.

The external force setting unit 160 sets the external force f according to the latest external force function f(x) set by the external force function setting unit 150 on the basis of the measured value of the myoelectric potential x measured by the myoelectric potential measurement unit 110.

The motor current control unit 170 controls the external force f applied to each leg through the orthosis 222 from the motor 220 by controlling supply current from the battery 200 to the motor 220 according to the set value of the external force f set by the external force setting unit 160.

Figure 3:
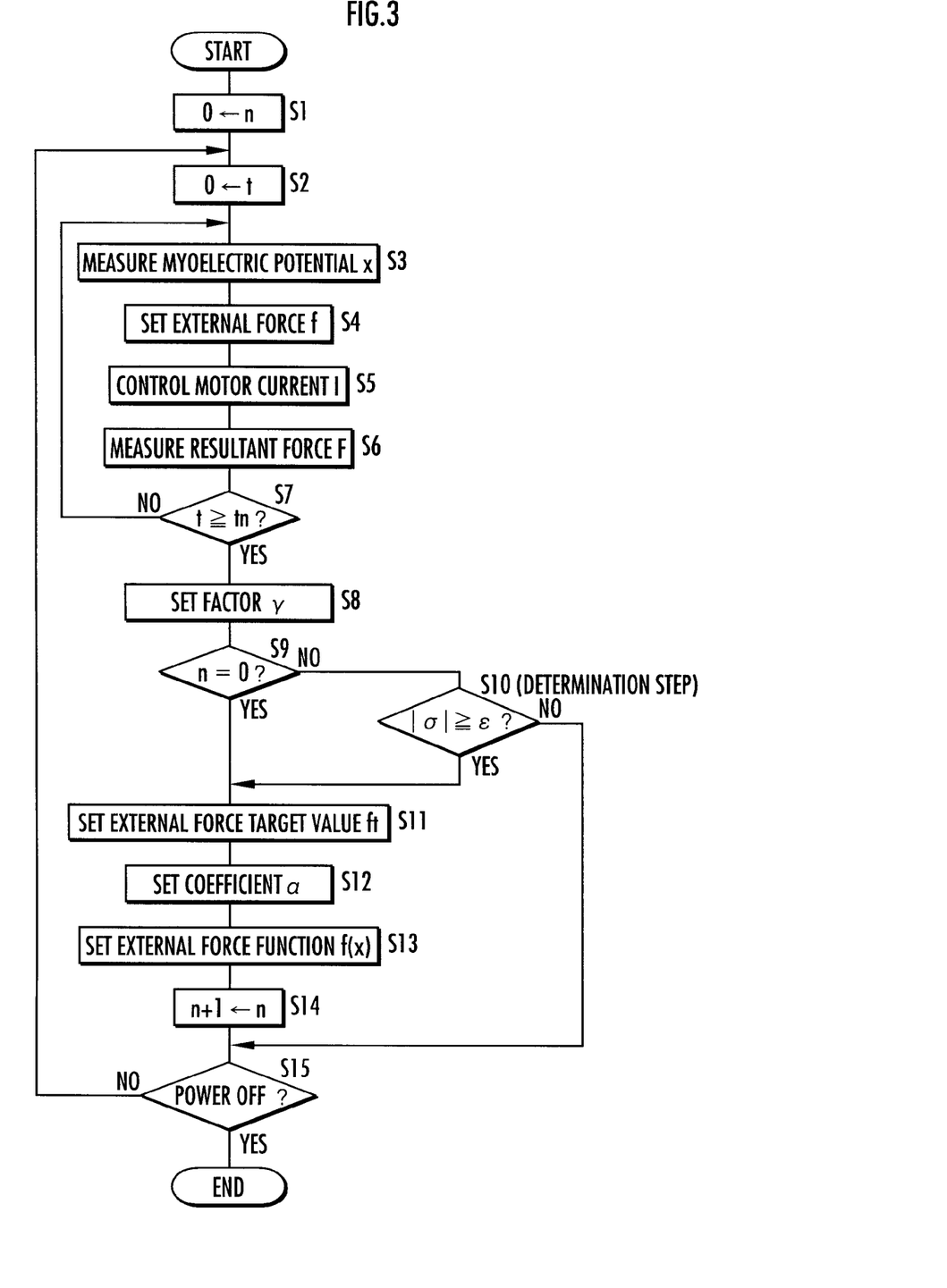
FIG. 3 is an explanatory diagram for external force control method according to one embodiment of the present invention.
Figure 4:
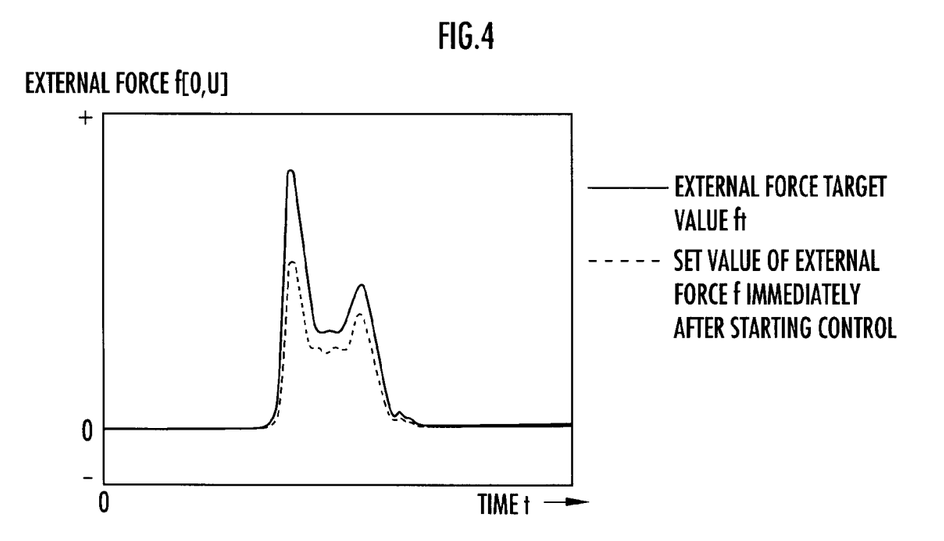
FIG. 4 is an explanatory diagram of an experimental result of the external force control method according to one embodiment of the present invention.

The following describes the external force control method performed by the external force control system 100 having the above configuration with reference to FIG. 3 and FIG. 4.

First, the control is started by OFF-to-ON switching of an ON/OFF switch (not shown) provided in the case 202. Thereby, the number of times n in setting the external force function f(x) is reset to "0" (S1) and the measurement time t of a timer (not shown) is reset to "0" (S2).

Furthermore, the myoelectric potential measurement unit 110 measures the value of the myoelectric potential x generated by the activities of the muscle fibers and varied along with the human locomotion or the like through the extensor surface electrodes 111 and the flexor surface electrodes 112 (S3). The myoelectric potential x includes an extensor potential $x_{i+}$ (i=1 (vastus medialis), 2 (vastus lateralis), 3 (rectus femoris)) measured through the extensor surface electrodes 111 and a flexor potential $x_{j-}$ (j=1 (semitendinosus), 2 (biceps femoris)) measured through the flexor surface electrodes 112. The measured values of the extensor potential $x_{i+}$ and the flexor potential $x_{j-}$ measured by the myoelectric potential measurement unit 110 are obtained by A/D-converting myoelectric signals detected by the extensor surface electrodes 111 and the flexor surface electrodes 112 after passing through a filter and an amplifier, converting them into absolute values, and passing them through a lowpass filter.

Furthermore, the external force setting unit 160 sets the external force f according to the external force function f(x) with the myoelectric potential x as a variable on the basis of the measured value of the myoelectric potential $x=(x_{1+}, x_{2+}, x_{3+}, x_{1-}, x_{2-})$ (S4). The first external force function f(x) is preset as shown in the following expression (1) on the basis of the empirical rule or the like and stored in the memory of the computer 10.

$$f(x) = h(x, \alpha)\gamma_t \quad (1)$$
$$\equiv (\Sigma_i \alpha_{i+} x_{i+} MA_{i+} + \Sigma_j \alpha_{j-} x_{j-} MA_{j-})\gamma_t$$

In the expression (1), the coefficient $\alpha=(\alpha_{1+}, \alpha_{2+}, \alpha_{3+}, \alpha_{1-}, \alpha_{2-})$ represents the relation between the myoelectric potential x and the external force f. The coefficients $\alpha_{i+}$ and $\alpha_{j-}$ are reverse in sign and the ratio between them is set such that the expression $\alpha_{i+}:\alpha_{j-}=1:-1/3$ is satisfied. $MA_{i+}$ is a moment arm of the extensor, in other words, a distance between the center of rotation of the joint and the position where the extensor is attached to the bone and varies with the flexion angle of the joint. Similarly, $MA_{j-}$ is a moment arm of the flexor, in other words, a distance between the center of rotation of the joint and the position where the flexor is attached to the bone and varies with the flexion angle of the joint. The extensor moment arm $MA_{i+}$ can be supposed to be equivalent to the flexor moment arm $MA_{j-}$.

Furthermore, the motor current control unit 170 controls the current I of the motor 220 according to the set value of the external force f set by the external force setting unit 160 (S5). This transmits the power of the motor 220 through the orthosis 222 and applies an external force (an external torque around the knee joint) f coincident with the set value to each human leg.

Moreover, the resultant force measurement unit 120 measures the resultant force F, namely, the sum of the internal torque and the external torque around the knee joint by using the inverse dynamics model that represents the human behaviors on the basis of the measured values of the primitive motion variables obtained by the sensors 121 to 127, more specifically, the tilt angle and the anteroposterior acceleration of the chest, the tilt angle of the waist, the anteroposterior acceleration and the vertical acceleration of the waist, the hip joint angle, and the knee joint angle (S6). Since the method of measuring the resultant force F using the inverse dynamics model is available only by adopting a method disclosed in Japanese Patent Laid-Open No. 2003-89083 or the like, its detailed description is omitted here. The resultant force F is defined with the direction of knee joint extension or the direction of moving the crus forward as positive.

Moreover, the factor setting unit 130 determines whether the timer measurement time t is equal to or greater than given time $t_n$. The given time $t_n$ can depend on the number of times n in setting the external force function f(x) such that $t_0$ is longer than $t_i$ ($i \neq 0$) or $t_0$ is shorter than $t_i$ ($i \neq 0$) or can be constant independently of the number of times n. If the time t is determined to be less than the given time $t_n$ (S7: NO), the measurement of the myoelectric potential x (S3), the setting of the external force f (S4), the control of the motor current (S5), and the measurement of the resultant force F (S6) are performed repeatedly. On the other hand, if the time t is determined to reach the given time $t_n$ (S7: YES), the factor setting unit 130 sets the factor γ according to the factor function γ(f, F) represented by the following expression (2) on the basis of the set value of the external force f (See S4) and the measured value of the resultant force F (See S6) (S8).

$$\gamma(f,F) = f/F \qquad (2)$$

The factor γ set according to the expression (2) determines the external force f applied to the human leg when the resultant force F is generated and can be referred to as "an assist ratio" because the external force f assists the motion.

Furthermore, the determination unit 140 determines whether the cumulative number of times n in setting the external force function f(x) is zero (S9). If the number of times n is determined to be zero (S9: YES), the external force function setting unit 150 sets the external force target value $f_t$ (S11), sets the coefficient α that represents the relation between the myoelectric potential x and the external force f (S12), and sets the external force function f(x) (S13).

On the other hand, unless the number of times n is determined to be zero (S9: NO), the determination unit 140 determines whether or not the deviation δ between the set value of the factor γ and its target value $\gamma_t$ is equal to or greater than the threshold ε (>0) (S10 (determination step)): if the deviation δ is determined to be equal to or greater than the threshold ε (S10: YES), the external force function setting unit 150 sets the external force target value $f_t$ (S11), sets the coefficient α that represents the relation between the myoelectric potential x and the external force f (S12), and sets the external force function f(x) (S13). The deviation δ can include a deviation at a single time point and a mean deviation or cumulative deviation at a plurality of time points or during a continuous time period.

More specifically, the external force function setting unit 150 sets the external force target value $f_t$ as the product of the measured value F of the resultant force (motion variable) F and the factor target value $\gamma_t$ (S11). Moreover, the external force function setting unit 150 sets the coefficient $\alpha = (\alpha_{1+}, \alpha_{2+}, \alpha_{3+}, \alpha_{1-}, \alpha_{2-})$ in such a way that the maximum set value of the external force f (See S4) is coincident with the maximum value $f_{tmax}$ of the external force target value $f_t$ (See S11), in other words, that the equation represented by the following expression (3) is satisfied by using the measured value of the myoelectric potential x obtained when the set value of the external force f is the maximum and the measured value of the factor γ (S12).

$$f_{tmax} = (\Sigma_i \alpha_{i+} x_{i+} MA_{i+} + \Sigma_j \alpha_{j-} x_{j-} MA_{j-}) \gamma_t / (1-\gamma) \qquad (3)$$

Thereafter, the external force function setting unit 150 sets the external force function f(x) according to the basic function F(x, α, γ) represented by the following expression (4) on the basis of the set value of the coefficient α and the measured value of the factor γ (S13).

$$F(x, \alpha, \gamma) = h(x, \alpha) \gamma_t / (1-\gamma) \qquad (4)$$
$$\equiv (\Sigma_i \alpha_{i+} x_{i+} MA_{i+} + \Sigma_j \alpha_{j-} x_{j-} MA_{j-}) \gamma_t / (1-\gamma)$$

After the setting of the external force function f(x), the setting number of times n is incremented by one (S14). Unless the ON/OFF switch (not shown) is switched from ON to OFF (S15: NO), the timer measurement time t is reset to zero (S2) and the measurement of the myoelectric potential x (S3) and subsequent processing are performed repeatedly.

According to the experimental result of the external force control method shown in FIG. 4, it has been shown that the set value (dashed line) of the external force f immediately after starting the control gradually approaches the external force target value $f_t$ (solid line) by the setting of the external force function f(x) (S12).

According to the external force control system 100 that performs the external force control method, the external force function f(x) is set in such a way that the set value of the external force f (See S4) is coincident with the external force target value $f_t$ (See S11) if the deviation δ is determined to be equal to or greater than the reference value ε (S10: YES) (S13). Moreover, the external force function f(x) is set according to the basic function F(x, α, γ) (See expression (4)) on the basis of the set value of the factor γ (See S8) that represents the relation between the external force f and the resultant force F and the set value of the coefficient α (See S12) that represents the relation between the myoelectric potential x and the external force f. This enables the control of the external force f based on the myoelectric potential x in such a way that the relation between the external force f and the resultant force F is coincident with the target relation $(\gamma_t = \gamma(f, F) = f/F)$, which depends on the factor target value $\gamma_t$, on the basis of the latest relation among the myoelectric potential x, the external force f, and the resultant force F, even if any change occurs in the contact condition or the like between the surface electrodes 111 and 112 and the leg.

Moreover, the first external force function f(x) does not yet reflect the actual relation between the external force f and the resultant force F. Therefore, in view of the fact that it is highly probable that the first set value of the external force f is far from the target relation between the external force f and the resultant force F, the external force function f(x) is set with the omission of the determination step (S10) if the number of times n in setting the external force function f(x) is "0." This enables the control of the external force f in such a way that the relation between the external force f and the resultant force F rapidly approaches the target relation.

In this embodiment, the animal as a target of the external force control has been a human being. In another embodiment, however, the animal can be any of all kinds of animals that make a movement along with the muscle fibers such as mammals including a monkey and a giraffe or fishes.

In this embodiment, the plurality of (three) extensor potentials $x_{i+}$ and the plurality of (two) flexor potentials $x_{j-}$ have been measured. In another embodiment, however, it is also possible to measure one extensor potential $x_+$ and one flexor potential $x_-$, to measure a plurality of extensor potentials $x_{i+}$ and one flexor potential $x_-$, or to measure one extensor potential $x_+$ and a plurality of flexor potentials $x_{j-}$. Moreover, the function $h(x, \alpha)$ included in the expressions (1) and (4) in each of these three alternative embodiments can be defined by the following expressions (5) to (7).

$$h(x,\alpha)=\alpha_+ x_+ MA_+ + \alpha_- x_- MA_- \quad (5)$$

$$h(x,\alpha)=\Sigma_i \alpha_{i+} x_{i+} MA_{i+} + \alpha_- x_- MA_- \quad (6)$$

$$h(x,\alpha)=\alpha_+ x_+ MA_+ + \Sigma_j \alpha_{j-} x_{j-} M_{j-} \quad (7)$$

Moreover, in this embodiment, the resultant force measurement unit 120 has measured the resultant force F as a motion variable, in other words, the sum of an internal force (a human voluntary knee joint torque) and the external force (a knee joint torque applied to the human leg) (See S6) on the basis of the outputs from the knee joint angle sensor 127 or the like and the "primitive motion variables" such as the knee joint angle and the angular velocity. In another embodiment, however, the resultant force measurement unit 120 can measure the external force F (motion variable) in various methods such as by measuring the external force F based on images captured by a camera (not shown) for taking photographs of human movements.

In this embodiment, the resultant force F, which is the sum of the internal torque (internal force) around the knee joint that arises in the leg due to the person's will and the external torque (external force) around the knee joint applied to the leg through the orthoses 222 by the motor 220, has been measured as "the motion variable." In another embodiment, however, it is also possible to measure a resultant torque of an internal torque and an external torque around a joint other than a hip joint, an ankle joint, an elbow joint, a shoulder joint and a knee joint, the rate of change in a joint angle such as a knee joint, joint angular velocity, joint angular acceleration, or joint torque, or any combination thereof as "the motion variable."

In this embodiment, the factor γ has been set (calculated) according to the factor function γ(f, F)=f/F in the form of the expression (2) (S8). In another embodiment, however, the factor γ can be set according to the factor function γ(f, F) of the external force f and the resultant force F in a different form from the above.

In this embodiment, the set value of the external force f has been used (See S4) at the setting of the factor γ (S8). In another embodiment, however, it is possible to measure the external force f based on an output from a strain gauge (not shown) attached to the orthosis 222 or an output from a current sensor (not shown) for measuring current of the motor 220 or the like and to use the measured value of the external force f at the setting of the factor γ. According to another embodiment, the factor γ is set on the basis of the measured value of the external force f, and therefore it is possible to control the external force f applied to each of the human legs after removing the effect of the deviation that may occur in the measured value of the external force f from the set value of the external force f.

In this embodiment, the factor γ has been set (calculated) whenever the timer measurement time t reaches the given time $t_n$ (See S7 and S8). In another embodiment, however, the external force control system 100 may include a vertical leg acceleration sensor for outputting a signal responsive to the vertical acceleration of the lower part of the leg and a counter for counting the number of times in the leg reaching the ground on the basis of the output from the vertical leg acceleration sensor, and the factor setting unit 130 may set (calculate) the factor γ whenever the counting number of times with the counter reaches a given number of times.

In this embodiment, the determination step (S10) has been omitted if the number of times n in setting the external force function f(x) is zero. In another embodiment, however, the determination step may be performed independently of the number of times n (even if the number of times n is zero).

In this embodiment, the coefficient α has been set in such a way that the maximum set value of the external force f is coincident with the maximum value $f_{tmax}$ of the external force target value $f_t$ (See S11 and S12). In another embodiment, however, the coefficient α may be set in such a way that the mean value or cumulative value of the set value of the external force f during a certain time period or at a plurality of time points is coincident with the mean value or cumulative value of the external force target value $f_t$ during the certain time period or at the plurality of time points.

In still another embodiment of the present invention, it is possible to omit the chest gyro sensor 121, the anteroposterior chest acceleration sensor 122, the waist gyro sensor 123, the anteroposterior waist acceleration sensor 124 and the vertical waist acceleration sensor 125. In addition, the external force control system 100 may include a motion state determination unit for determining the human motion state on the basis of the output from the hip joint angle sensor 126 and an output from the knee joint angle sensor 127, and the resultant force measurement unit 120 may read (measure) the resultant force F stored in the memory with being associated with the motion state determined by the motion state determination unit on the basis of the motion state.

In another embodiment described above, a concrete determination method of the motion state is available only by adopting a method disclosed in Japanese Patent Laid-Open No. 2003-116893. Therefore, its detailed description is omitted here. The motion state determination unit determines which is the human motion state among a plurality of motion states including "a level walking state" where a person is walking on a level ground or on a sloping ground whose slope is vanishingly gentle, "a downward walking state" where the person is descending stairs or a sloping road, "an upward walking state" where the person is ascending stairs or a sloping road, "a rise-from-chair state" where the person is rising from a chair, and "a sit-on-chair state" where the person is sitting on a chair from a standing position.

In still another embodiment of the present invention, the external force control system 100 may include a motion state determination unit to set the external force function f(x) according to a basic function F(x, α, γ) set for each motion state based on the motion state determined by the motion state determination unit and stored in the memory (S12). Moreover, in further another embodiment, the external force control system 100 may include a motion state determination unit, the determination unit 140 may make determination on the basis of the factor target value $\gamma_t$ set for each motion state based on the motion state determined by the motion state determination unit and stored in the memory (S10), and the external force function setting unit 150 may set the external force function f(x) after setting the coefficient α on the basis of the factor target value $\gamma_t$ set for each motion state according to the motion state determined by the motion state determination unit (S11, S12).

According to the above embodiment, it is possible to achieve the appropriate external force f applied to a user's leg with consideration given to the user's (human) motion state.

In still another embodiment of the present invention, the determination unit 140 may determine whether the deviation δ is less than the threshold ε according to the threshold ε that depends on the difference between positive or negative in the deviation δ. According to another embodiment described above, it is possible to control the external force f in such a way that if the instability level of the motion of the animal undergoing the external force f depends on whether the deviation δ between the set value of the factor γ and its target value $\gamma_t$ is positive or negative, the motion of the animal is stable with consideration given to the difference between them.

What is claimed is:

1. An external force control method for controlling an external force applied to a first living body portion of an animal through an orthosis attached to the first living body portion of the animal that makes a movement along with the activities of animal muscle fibers, the method comprising:

a myoelectric potential measurement step of measuring a myoelectric potential x that occurs in a second living body portion of the animal;

an external force setting step of setting a value of an external force f applied to the first living body portion of the animal through the orthosis according to an external force function f(x) with the myoelectric potential x as a variable on the basis of the measured value of the myoelectric potential x;

a motion variable measurement step of measuring a motion variable y varying with the motion of the animal under the condition of the external force applied through the orthosis;

a factor setting step of setting a value of a factor γ according to a factor function γ(f, y) with the external force f and the motion variable y as variables on the basis of the set value of the external force f and the measured value of the motion variable y;

a determination step of determining whether a deviation δ between the set value of the factor γ and target value $\gamma_t$ thereof is less than a reference value ε; and an external force function setting step of setting a new external force function f(x) in such a way that the set value of the factor γ approaches the target value $\gamma_t$ if the deviation δ is determined to be equal to or greater than the reference value ε in the determination step, wherein the motion variable measurement step comprises measuring the resultant force of an internal force, which is a force exerted on the orthosis by the first living body portion caused by activities of animal muscle fibers in at least the second living body portion of the animal, and an external force, caused by a motion of an actuator and applied through the orthosis to the first living body portion of the animal, as the motion variable y; and the factor setting step comprises setting the ratio of the external force f to the resultant force of the internal force and the external force of the animal as the factor γ(0≦γ<1).

2. The external force control method according to claim 1, wherein the external force function setting step comprises setting a value of a coefficient α that represents the relation between the myoelectric potential x and the external force f and setting the external force function f(x) according to a basic function F(x, α) with the myoelectric potential x and the coefficient α as variables on the basis of the set value of the coefficient α.

3. The external force control method according to claim 1, wherein the external force function setting step comprises finding the external force target value $f_t$ according to the factor function γ(f, y) on the basis of the measured value of the motion variable y and the target value $\gamma_t$ of the factor γ and setting the external force function f(x) in such a way that the external force f approaches the external force target value $f_t$.

4. The external force control method according to claim 3, wherein the external force function setting step comprises setting the external force function f(x) in such a way that the maximum measured value of the external force f approaches the maximum value of the external force target value $f_t$.

5. The external force control method according to claim 1, wherein the determination step is omitted and the external force function setting step is performed after the first external force setting step.

6. The external force control method according to claim 1, wherein the motion variable measurement step comprises measuring a primitive motion variable varying with the motion of the animal and measuring the motion variable according to an inverse dynamics model that represents the behaviors of the animal on the basis of the measured value of the primitive motion variable.

7. The external force control method according to claim 1, further comprising a motion state determination step of determining the motion state of the animal according to a given correspondence between a primitive motion variable and the motion state of the animal on the basis of the measured value of the primitive motion variable after measuring the primitive motion variable varying with the motion of the animal, wherein the motion variable measurement step comprises measuring the motion variable y according to a given correspondence between the motion state of the animal and the motion variable on the basis of the motion state determined in the motion state determination step.

8. The external force control method according to claim 1, further comprising a step of measuring the external force f, wherein the factor setting step comprises setting a value of the factor γ according to the factor function γ(f, y) with the external force f and the motion variable y as variables on the basis of the measured value of the external force f, instead of the set value of the external force f, and the measured value of the motion variable y.

9. The external force control method according to claim 1, further comprising a motion state determination step of determining the motion state of the animal according to a given correspondence between the primitive motion variable and the motion state of the animal on the basis of the measured value of the primitive motion variable after measuring the primitive motion variable varying with the motion of the animal, wherein the external force function setting step comprises setting a new external force function f(x) responsive to each motion state determined in the motion state determination step.

10. The external force control method according to claim 9, wherein:
- the determination step comprises determining whether the deviation $\delta$ is less than the reference value $\epsilon$ on the basis of the factor target value $\gamma_t$ set for each motion state according to the motion state determined in the motion state determination step; and
- the external force function setting step comprises setting a new external force function f(x) on the basis of the factor target value $\gamma_t$ set for each motion state according to the motion state determined in the motion state determination step.

11. The external force control method according to claim 1, wherein the determination step comprises determining whether the deviation $\delta$ is less than a threshold $\epsilon$ according to the threshold $\epsilon$ depending on whether the deviation $\delta$ is positive or negative.

12. An external force control system for controlling an external force applied to a first living body portion of an animal through an orthosis attached to the first living body portion of the animal that makes a movement along with the activities of muscle fibers, the system comprising:
- myoelectric potential measurement means for measuring a myoelectric potential x that occurs in a second living body portion of the animal;
- external force setting means for setting a value of an external force f applied to the first living body portion of the animal through the orthosis according to an external force function f(x) with the myoelectric potential x as a variable on the basis of the measured value of the myoelectric potential x measured by the myoelectric potential measurement means;
- motion variable measurement means for measuring a motion variable y varying with the motion of the animal under the condition of the external force applied through the orthosis, wherein the motion variable y is a resultant force of an internal force, which is a force exerted on the orthosis by the first living body portion caused by activities of animal muscle fibers in at least the second living body portion of the animal, and the external force caused by a motion of an actuator and applied to the first living body portion of the animal;
- factor setting means for setting a value of a factor $\gamma$ according to a factor function $\gamma$(f, y) with the external force f and the motion variable y as variables on the basis of the set value of the external force f set by the external force setting means and the measured value of the motion variable y measured by the motion variable measurement means;
- determination means for determining whether a deviation $\delta$ between the set value of the factor $\gamma$ set by the factor setting means and target value $\gamma_t$ thereof is less than a reference value $\epsilon$, and
- external force function setting means for setting a new external force function f(x) in such a way that the set value of the factor $\gamma$ approaches the target value $\gamma_t$ if the deviation $\delta$ is determined to be equal to or greater than the reference value $\epsilon$ by the determination means.

13. An external force control program for providing a computer with functions for controlling an external force applied to a first living body portion of an animal through an orthosis attached to the first living body portion of the animal that makes a movement along with the activities of muscle fibers, the program providing the computer with:
- a myoelectric potential measurement function of measuring a myoelectric potential x that occurs in a second living body portion of the animal;
- an external force setting function of setting a value of an external force f applied to the first living body portion of the animal through the orthosis according to an external force function f(x) with the myoelectric potential x as a variable on the basis of the measured value of the myoelectric potential x;
- a motion variable measurement function of measuring a motion variable y varying with the motion of the animal under the condition of the external force applied through the orthosis, wherein the motion variable y is a resultant force of an internal force, which is a force exerted on the orthosis by the first living body portion caused by activities of animal muscle fibers in at least the second living body portion, and the external force caused by a motion of an actuator and applied through the orthosis to the first living body portion of the animal;
- a factor setting function of setting a value of a factor $\gamma$ according to a factor function $\gamma$ (f, y) with the external force f and the motion variable y as variables on the basis of the set value of the external force f and the measured value of the motion variable y;
- a determination function of determining whether a deviation $\delta$ between the set value of the factor $\gamma$ and target value $\gamma_t$ thereof is less than a reference value $\epsilon$; and
- an external force function setting function of setting a new external force function f(x) in such a way that the set value of the factor $\gamma$ approaches the target value $\gamma_t$ if the deviation $\delta$ is determined to be equal to or greater than the reference value $\epsilon$ by the determination function.

14. The external force control method according to claim 1, wherein the first and second living body portions compose a common living body portion of the animal.

15. The external force control method according to claim 14, wherein the animal has a living leg as the common living body portion.

16. The external force control method according to claim 12, wherein the first and second living body portions compose a common living body portion of the animal.

17. The external force control method according to claim 16, wherein the animal has a living leg as the common living body portion.

18. The external force control method according to claim 13, wherein the first and second living body portions compose a common living body portion of the animal.

19. The external force control method according to claim 18, wherein the animal has a living leg as the common living body portion.

* * * * *